US012727785B2

(12) United States Patent
Shirasaka et al.

(10) Patent No.: US 12,727,785 B2
(45) Date of Patent: Sep. 8, 2026

(54) STATE DETERMINATION METHOD, STATE DETERMINATION DEVICE, STATE DETERMINATION SYSTEM, AND RECORDING MEDIUM

(71) Applicant: SEKISUI CHEMICAL CO., LTD., Osaka (JP)

(72) Inventors: Yasuyuki Shirasaka, Osaka (JP); Tetsuhiro Katou, Osaka (JP); Taehyung Cho, Osaka (JP); Yuuta Katsurayama, Osaka (JP); Ryousuke Takahashi, Osaka (JP); Yuri Hirono, Osaka (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 846 days.

(21) Appl. No.: 17/781,835

(22) PCT Filed: Dec. 2, 2020

(86) PCT No.: PCT/JP2020/044891
§ 371 (c)(1),
(2) Date: Jun. 2, 2022

(87) PCT Pub. No.: WO2021/112131
PCT Pub. Date: Jun. 10, 2021

(65) Prior Publication Data

US 2023/0000394 A1 Jan. 5, 2023

(30) Foreign Application Priority Data

Dec. 4, 2019 (JP) ................................ 2019-219768

(51) Int. Cl.
*A61B 5/11* (2006.01)
*A61B 5/00* (2006.01)

(52) U.S. Cl.
CPC .......... *A61B 5/1116* (2013.01); *A61B 5/6892* (2013.01); *A61B 5/7225* (2013.01)

(58) Field of Classification Search
None
See application file for complete search history.

(56) References Cited

U.S. PATENT DOCUMENTS

2004/0112151 A1 6/2004 Maxwell et al.
2016/0007887 A1 1/2016 Shimizu
(Continued)

FOREIGN PATENT DOCUMENTS

CN 108289638 7/2018
CN 109589137 4/2019
(Continued)

OTHER PUBLICATIONS

International Search Report issued Mar. 2, 2021 in corresponding International Application No. PCT/JP2020/044891.
(Continued)

*Primary Examiner* — Benjamin S Melhus
(74) *Attorney, Agent, or Firm* — Wenderoth, Lind & Ponack, L.L.P.

(57) ABSTRACT

A state determination method, a state determination device, a state determination system, and a recording medium are provided for determining a state of a living body based on electrical signal according to a detected vibration. A state determination device 2 acquires electrical signal according to a detected vibration, and operates: a rectification unit (step S2); an envelope detection unit to derive an envelope from the rectified electrical signal (step S3); and a state determination unit to determine the state of the living body based on the derived envelope (step S4). The state determination device 2 that has determined the state of the living body outputs a determination result (step S5).

15 Claims, 11 Drawing Sheets

(56) References Cited

U.S. PATENT DOCUMENTS

| | | | | |
|---|---|---|---|---|
| 2019/0076084 | A1 | 3/2019 | Kanegae et al. | |
| 2019/0175103 | A1 | 6/2019 | Kogure et al. | |
| 2021/0106256 | A1 | 4/2021 | Kogure et al. | |
| 2022/0029086 | A1* | 1/2022 | Shimizu .................. | A61B 5/11 |
| 2023/0037703 | A1 | 2/2023 | Kogure et al. | |

FOREIGN PATENT DOCUMENTS

| | | |
|---|---|---|
| CN | 110215214 | 9/2019 |
| JP | 5-95935 | 4/1993 |
| JP | 2004-261542 | 9/2004 |
| JP | 2004-533281 | 11/2004 |
| JP | 2007-202847 | 8/2007 |
| JP | 2008-110031 | 5/2008 |
| JP | 4342298 | 10/2009 |
| JP | 2014-195543 | 10/2014 |
| JP | 2015-008920 | 1/2015 |
| JP | 2015-154926 | 8/2015 |
| JP | 6311215 | 4/2018 |
| JP | 2019-98068 | 6/2019 |
| JP | 2019-098069 | 6/2019 |
| KR | 10-2018-0108664 | 10/2018 |
| TW | M569913 | 11/2018 |
| TW | 201941145 | 10/2019 |

OTHER PUBLICATIONS

Office Action issued Aug. 2, 2009 in Chinese Patent Application No. 202080083284.9.

* cited by examiner

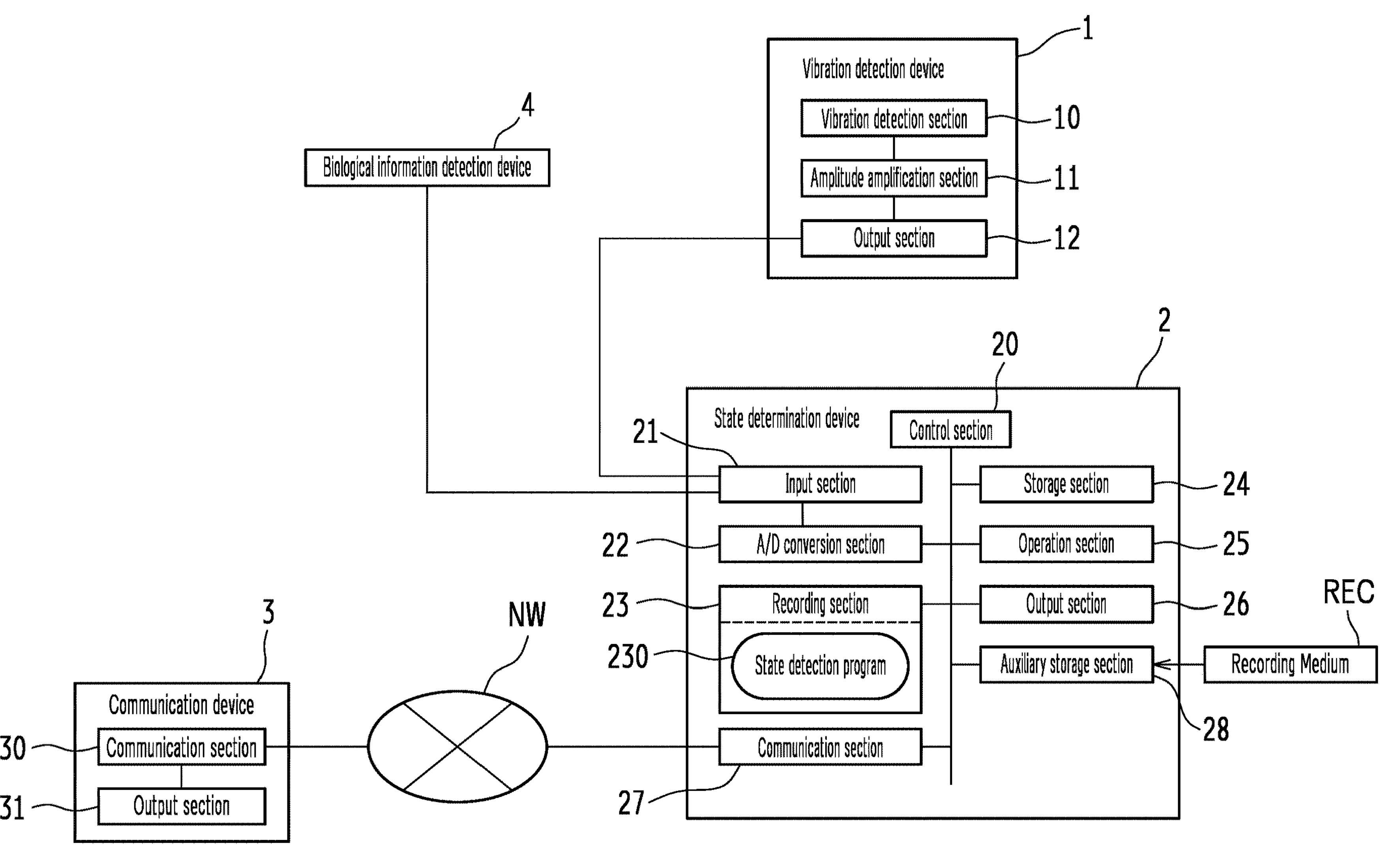
FIG.2
Biological information detection device
4
Vibration detection device
Vibration detection section
Amplitude amplification section
Output section
1
10
11
12
State determination device
Control section
Input section
A/D conversion section
Recording section
State detection program
Communication section
Storage section
Operation section
Output section
Auxiliary storage section
Recording Medium
REC
2
20
21
22
23
230
24
25
26
27
28
NW
Communication device
Communication section
Output section
3
30
31

STATE DETERMINATION METHOD, STATE DETERMINATION DEVICE, STATE DETERMINATION SYSTEM, AND RECORDING MEDIUM

TECHNICAL FIELD

The present invention relates to a state determination method for determining the state of a living body, a state determination device to which the method is applied, a state determination system including the state determination device, and a recording medium storing a state determination program to realize the state determination device.

BACKGROUND ART

In a facility such as a hospital, a nursing home or a nursing facility, a parson in charge (a nurse or a caregiver) looks around the facility to confirm the state of each care recipient (a patient or a resident), for example, whether he/she is in the bed in a patient room or getting out from the bed. In order to support such a patrol work, the Applicant of the present invention has proposed, for example, a living body detection system to be placed on a bed, which is capable of detecting whether a care recipient is present or not (see, for example, Patent Document 1).

PATENT ART DOCUMENT

Patent Document

[Patent Document 1] JP 2015-154926 A

SUMMARY OF THE INVENTION

Problem to be Solved by the Invention

Patent Document 1 proposes an excellent living body detection system. However, for the purpose of further enriching the quality of care and/or nursing care, now there is a demand for detecting how the state of a care recipient on the bed is.

The present invention was made in consideration of the above circumstances, a principal object of which is to provide a state determination method that is capable of determining a state of a living body.

Also, another object of the present invention is to provide a state determination device to which the state determination method of the present invention is applied.

Furthermore, another object of the present invention is to provide a state determination system including the state determination device of the present invention.

Furthermore, another object of the present invention is to provide a recording medium storing the state determination program to realize the state determination device of the present invention.

Means for Solving the Problem

In order to solve the above problem, a state determination method of the present invention includes the steps of: rectifying electrical signal according to a vibration generated by a living body; deriving an envelope from the rectified electrical signal; and determining a state of the living body based on the derived envelope.

Also in the state determination method of the present invention, a position of the living body is determined as the state of the living body.

Also in the state determination method of the present invention, the position of a person as the living body is determined by comparing a value indicated by the derived envelope to at least one predetermined threshold value, and the position of the person as a determination result includes at least a lying position or a sitting position.

Also in the state determination method of the present invention, the at least one predetermined threshold value includes a plurality of predetermined threshold values, and the plurality of predetermined threshold values includes a bed-entry determination threshold value to determine a bed-entry motion of the person and a get-up determination threshold value to determine a get-up motion of the person who is in a bed. The bed-entry determination threshold value is set to a value larger than the get-up determination threshold value.

Also in the state determination method of the present invention, it is determined that the person is absent when the value indicated by the envelope remains smaller than the bed-entry determination threshold value and the get-up determination threshold value for a predetermined period of time, and furthermore it is determined that the bed-entry motion is taken when the value indicated by the envelope becomes larger than the get-up determination threshold value and the bed-entry determination threshold value after it is determined that the person is absent.

Also in the state determination method of the present invention, it is determined that the position of the person is the lying position when the value indicated by the envelope becomes larger than the get-up determination threshold value but smaller than the bed-entry determination threshold value after it is determined that the person takes the bed-entry motion, and furthermore it is determined that the position of the person is the sitting position when the value indicated by the envelope becomes smaller than the get-up determination threshold value after it is determined that the person is in the lying position.

Also in the state determination method of the present invention, the envelope is derived by passing the electrical signal at a predetermined frequency band.

Also in the state determination method of the present invention, the envelope is derived by calculating a moving average of the electrical signal.

Also in the state determination method of the present invention, an A/D conversion section is used, which converts the electrical signal acquired as the analog signal according to the vibration into the digital electrical signal. The converted digital electrical signal is rectified.

Furthermore, a state determination device of the present invention includes a computer having a control section and a recording section. In the state determination device, the recording section records a program to cause the computer to operate: a rectification unit to rectify electrical signal according to a vibration generated by a living body; an envelope detection unit to derive an envelope from the rectified electrical signal; and a determination unit to determine a state of the living body based on the derived envelope.

Also in the state determination device of the present invention, the determination unit determines a position of the living body as the state of the living body.

Also in the state determination device of the present invention, the determination unit determines the position of a person as the living body by comparing a value indicated by the envelope derived from the envelope detection unit to at least one predetermined threshold value, and the position of the person, which is a determination result, includes at least a lying position or a sitting position.

Also in the state determination device of the present invention, the at least one predetermined threshold value includes a plurality of predetermined threshold values, and the plurality of predetermined threshold values includes a bed-entry determination threshold value to determine a bed-entry motion of the person and a get-up determination threshold value to determine a get-up motion of the person in the bed. The bed-entry determination threshold value is set to a value larger than the get-up determination threshold value.

Also in the state determination device of the present invention, the determination unit determines that the person is absent when the value indicated by the envelope remains smaller than the bed-entry determination threshold value and the get-up determination threshold value for a predetermined period of time, and furthermore the determination unit determines that the bed-entry motion is taken when the value indicated by the envelope becomes larger than the get-up determination threshold value and the bed-entry determination threshold value after it is determined that the person is absent.

Also in the state determination device of the present invention, the determination unit determines that the position of the person is the lying position when the value indicated by the envelope becomes larger than the get-up determination threshold value but smaller than the bed-entry determination threshold value after it is determined that the person takes the bed-entry motion, and furthermore the determination unit determines that the position of the person is the sitting position when the value indicated by the envelope becomes smaller than the get-up determination threshold value after it is determined that the person is in the lying position.

Also in the state determination device of the present invention, the envelope detection unit derives the envelope by passing the electrical signal at a predetermined frequency band.

Also in the state determination device of the present invention, the envelope detection unit derives the envelope by calculating a moving average of the electrical signal.

Also the state determination device of the present invention further includes an A/D conversion section that converts the electrical signal acquired as the analog signal according to the vibration into digital electrical signal. The rectification unit rectifies the converted digital electrical signal.

Furthermore, a state determination system of the present invention includes: a vibration detection device including a detection section that detects a vibration and an output section that outputs electrical signal according to the detected vibration; and the state determination device as described above. In the state determination device, the state of the living body is determined based on the electrical signal that is output from the vibration detection device.

Also in the state determination system of the present invention, the detection section of the vibration detection device has a sheet-like shape.

Also a state determination program of the present invention causes a computer acquiring electrical signal according to a detected vibration to determine the state of the living body. The state determination program causes the computer to execute the steps of: rectifying the electrical signal according to the vibration; deriving an envelope from the rectified electrical signal; and determining the state of the living body based on the derived envelope.

Furthermore, a recording medium of the present invention is a recording medium in which a state determination program is recorded, the state determination program to cause a computer acquiring electrical signal according to a detected vibration to determine the state of the living body. The state determination program causes the computer to execute the steps of: rectifying the electrical signal according to the vibration; deriving an envelope from the rectified electrical signal; and determining the state of the living body based on the derived envelope.

Also in the present invention, the state determination device is disclosed, in which the determination criterion at the time of determining whether the value indicated by the envelope is larger/smaller than the bed-entry determination threshold value/the get-up determination threshold value is whether the state remains for a predetermined period of time.

Also in the present invention, the state determination device is disclosed, in which the electrical signal according to the vibration is amplified, so that the amplification rate is adjusted according to the living body whose state is determined and/or the environment under which the state is determined.

Also in the present invention, the state determination device is disclosed, in which the bed-entry determination threshold value or the get-up determination threshold value is changed for a predetermined period of time according to the state of the living body.

Also in the present invention, the state determination system is disclosed, which includes a detection device to detect biological information. The state determination device determines the state of the living body using also the biological information detected by the detection device.

Effects of the Invention

In the state determination method, the state determination device, the state determination system and the recording medium of the present invention, the state of a living body is determined by the envelope of the electrical signal according to the detected vibration. In this way, the present invention provides excellent effects such as determination of a living body (e.g. a care recipient) in a facility.

BRIEF DESCRIPTION OF THE DRAWINGS

FIG. 2 is a block diagram exemplarily illustrating configurations of respective devices provided in the state determination system of the present invention.

MODE FOR CARRYING OUT THE INVENTION

Hereinafter, an embodiment of the present invention will be described with reference to the drawings. Note that the embodiment described below is an example to realize the present invention, and thus it does not limit the technical scope of the present invention.

<State Determination System>

Figure 1:
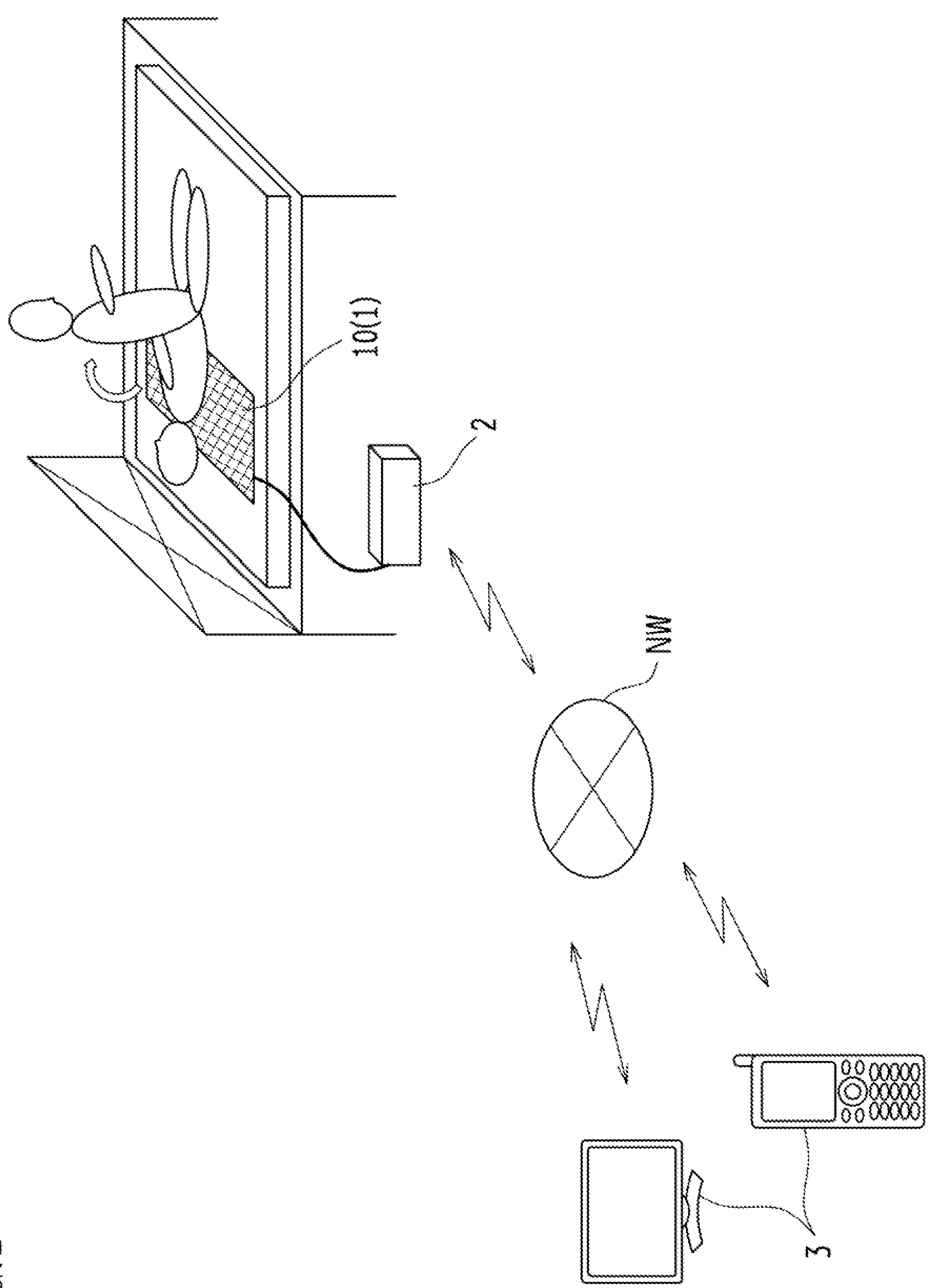
FIG. 1 is a schematic diagram exemplarily illustrating a configuration of a state determination system of the present invention.

FIG. 1 is a schematic diagram exemplarily illustrating a configuration of a state determination system of the present invention. The state determination system of the present invention is to be equipped in a facility such as a hospital, a nursing home or a nursing facility. The facility has rooms such as hospital rooms and care rooms where care recipients (patients or residents) reside. In these rooms, beds are placed for the care recipients. The facility also has waiting rooms (e.g. nurse's stations) where staff such as nurses, caregivers and doctors are on call to care for the care recipients.

A vibration detection device 1 is provided on a bed used by the care recipient. The vibration detection device 1 includes a vibration detection section 10 using a sheet-like vibration sensor, which amplifies and outputs electrical signal according to a detected vibration. The vibration detection section 10 of the vibration detection device 1 is placed, for example, on the bed used by the care recipient, specifically, on an upper surface or a lower surface of a mattress of the bed. On the mattress and the vibration detection section 10, a sheet or the like is put, as needed. FIG. 1 exemplarily shows a state in which the care recipient on the mattress and the vibration detection section 10 gets up from a lying position to take a sitting position. In the present invention, the state of the lying position means the state in which the care recipient is lying down on the bed, including a supine position, a lateral position, and a prone position. The state of the sitting position means the state in which the care recipient is raising his/her upper body on the bed.

The vibration detection device 1 is connected to a state determination device 2. The electrical signal that is output from the vibration detection device 1 is input into the state determination device 2 via a communication line. As devices capable of communicating with the state determination device 2, various kinds of communication devices 3 are used, which include a nurse call receiver carried by a nurse, a monitor equipped in the nurse's station, and a mobile phone carried by an external person involved. The state determination device 2 and the communication device 3 are communicably connected to each other via a communication network NW such as a wireless LAN (Local Area Network), a wired LAN, a WAN (Wide Area Network), or a dedicated communication line.

<Configurations of Respective Devices>

Here, hardware configurations of the respective devices provided in the state determination system of the present invention will be described. FIG. 2 is a block diagram exemplarily illustrating configurations of the respective devices provided in the state determination system of the present invention. The state determination system includes various devices such as the vibration detection device 1, the state determination device 2 connected to the vibration detection device 1, the communication device 3 capable of communicating with the state determination device 2, and a biological information detection device 4 that can be connected to the state determination device 2.

Apart from the vibration detection section 10 using the sheet-like vibration sensor, the vibration detection device 1 also includes various sections such as an amplitude amplification section 11 and an output section 12. The vibration detection section 10 detects a vibration of a living body such as a care recipient, and converts the detected vibration into the analog electrical signal so as to output the analog electrical signal to the amplitude amplification section 11. The amplitude amplification section 11 is a signal amplifier that amplifies the voltage of the electrical signal. Thus, the amplitude amplification section 11 amplifies the voltage amplitude of the analog electrical signal that is input from the vibration detection section 10 so as to output the thus amplified analog electrical signal to the output section 12. The output section 12 outputs, via a connection line, the analog electrical signal amplified by the amplitude amplification section 11 to the state determination device 2.

The state determination device 2 is a device made by use of various kinds of computers such as a signal processing computer and a personal computer. The state determination device 2 includes various sections such as a control section 20, an input section 21, an A/D conversion section 22, a recording section 23, a storage section 24, an operation section 25, an output section 26, a communication section 27, and an auxiliary storage section 28.

The control section 20 includes various circuits such as an information processing circuit, a timing circuit, and a register circuit. The control section 20 is a processor such as a CPU (Central Processing Unit) that executes processing for controlling the respective sections of the device.

The input section 21 is an interface device including various adapters and a control circuit so as to receive input of the analog electrical signal transmitted from the vibration detection device 1 via the connection line.

The A/D conversion section 22 is a converter that converts, into the digital electrical signal, the analog electrical signal that is received by and input into the input section 21.

The recording section 23 is a circuit configured using: non-volatile memories such as a hard disk, RAID (Redundant Arrays of Inexpensive Disks), and a flash memory; and volatile memories such as various RAMs (Random Access Memories), so as to record various kinds of information. The recording section 23 records programs such as a basic program (OS: Operating System) and an application program that is operated in the basic program. Various programs such as a state determination program 230 to realize the state determination device 2 are recorded as the application programs. Also, the recording section 23 records various kinds of data such as master data on various threshold values used by the state determination program 230, and actual data recording a processing history.

The storage section 24 is a circuit configured using volatile memories so as to temporarily store data generated at the time of executing the respective programs. For the sake of understandability, the recording section 23 and the storage section 24 are shown as different circuits. However, they may be configured as a single circuit. Alternatively, they may complement each other to perform their functions.

The operation section 25 is an operation device such as a touch screen or a push button, which receives input of operation to the state determination device 2. When the state determination device 2 is configured using a computer such as a personal computer, operation devices such as a keyboard and a mouse may be used as the operation section 25.

The output section 26 is an output device such as a liquid crystal display or a speaker. The operation section 25 and the output section 26 may be a liquid crystal touch screen made by laminating, for example, a thin-plate like liquid crystal display and a thin-plate like touch screen.

The communication section 27 is an interface device such as an antenna, a LAN adapter, a control circuit or the like, which performs a wireless communication or a wired communication with the communication device 3 via the communication network NW.

The auxiliary storage section 28 is an interface device such as a drive or a slot so as to read programs and data from a portable recording medium REC (such as a CD-ROM, a DVD-ROM and a semiconductor memory) in which data and programs such as the state determination program 230 are recorded.

The computer configured as described above is controlled by the control section 20 so as to, for example, read the respective programs such as the state determination program 230 recorded in the portable recording medium REC, and to record the read programs in the recording section 23. Then, the computer reads the respective programs such as the state determination program 230 recorded in the recording section 23 and stores appropriately respective kinds of information in the storage section 24. Thus, the computer operates as the state determination device 2 by executing respective procedures such as rectification processing, envelope detection processing, state determination processing, determination result output processing and the like.

The communication device 3 includes sections such as a communication section 30 that performs communication with the state determination device 2 via the communication network NW, and an output section 31 that performs respective kinds of output. Examples of the output from the output section 31 include: light output; image display; audio output; ringing; and vibrating.

The biological information detection device 4 is a device that detects biological information on the care recipient such as a heart rate, a respiratory rate and a pulse. The biological information detection device 4 is used as needed.

<Processing of Respective Devices>

Here, processing of the respective devices in the state determination system of the present invention will be described. The vibration detection device 1 detects, by the vibration detection section 10, a vibration related to a living body such as a care recipient so as to convert the detected vibration into the analog electrical signal. Furthermore, the vibration detection device 1 amplifies, by the amplitude amplification section 11, the voltage of the analog electrical signal according to the vibration so as to output the amplified analog electrical signal to the state determination device 2 by the output section 12.

Figure 3:
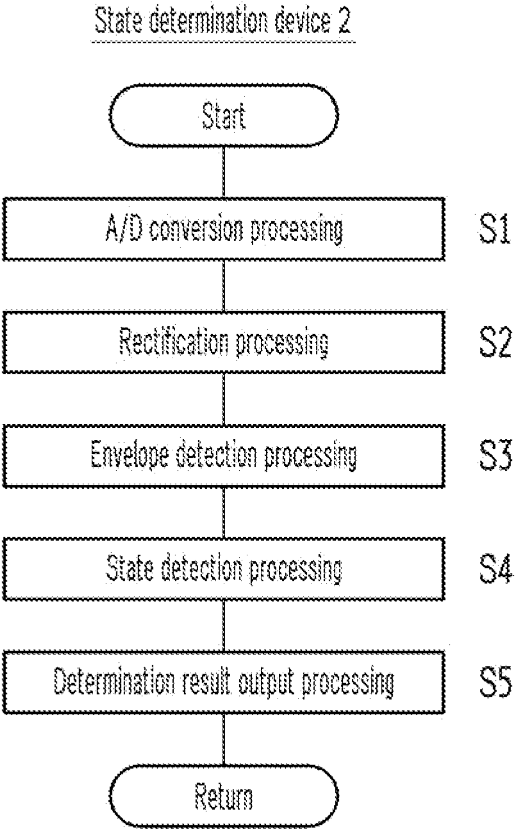
FIG. 3 is a flowchart indicating one example of processing by a state determination device of the present invention.

FIG. 3 is a flowchart indicating one example of processing by the state determination device 2 of the present invention. The state determination device 2 receives, by the input section 21, input of the analog electrical signal from the vibration detection device 1, and performs, by the A/D conversion section 22, A/D conversion processing to convert the received analog electrical signal into the digital electrical signal (step S1). In the A/D conversion processing in step S1, the received analog electrical signal is sampled at a predetermined sampling interval of, for example, 10 ms so as to convert the analog electrical signal into the digital electrical signal of, for example, 16 bit.

In step S1, the digital electrical signal after conversion by the A/D conversion section 22 is, for example, 16-bit digital data. The control section 20 provided in the state determination device 2 executes programs such as the state determination program 230 so that the digital electrical signal as digital data is processed by algorithm including procedures such as rectification processing, envelope detection processing, state determination processing, and determination result output processing.

The control section 20 performs rectification processing to the digital electrical signal after subjected to the A/D conversion processing (step S2). The rectification processing in step S2 is processing to convert the digital electrical signal into a pulsating current by the rectification processing such as half-wave rectification and full-wave rectification.

The control section 20 performs envelope detection processing to the digital electrical signal after subjected to the rectification processing so as to derive the envelope from the rectified digital electrical signal (step S3). The envelope detection processing in step S3 is processing to smooth the digital electrical signal converted into the pulsating current. Examples of the method for smoothing by the envelope detection processing include any one or any combination of the following: moving-average processing; BPF (band-pass filter) processing; and LPF (low-pass filter) processing. The moving-average processing is processing to derive the envelope by calculating the average of predetermined sampling number of signal values. The BPF processing is digital filter processing to pass the digital electrical signal at a predetermined frequency band and cutoff the digital electrical signal at the frequency band other than that at which the digital electrical signal is allowed to pass. The BPF processing is performed by filter processing such as FIR (finite impulse response) filter and IIR (infinite impulse response) filter. The LPF processing is digital filter processing to pass the digital electrical signal at a frequency band smaller than a certain frequency and cutoff the digital electrical signal at the frequency band other than that at which the digital electrical signal is allowed to pass. The LPF processing is performed by filter processing such as FIR filter and IIR filter.

After the envelope detection processing, the control section 20 performs state determination processing to determine the state of the living body based on the derived envelope (step S4). The state determination processing in step S4 is processing to determine the state of the living body by comparing the signal value indicated by the envelope derived from the envelope detection processing to the respective threshold values recorded in advance in the recording section 23. By comparing the signal value indicated by the envelope to the respective threshold values, it is determined whether a care recipient as the living body is present or absent, and how his/her state such as his/her position is. The position to be determined as the state means a position such as a lying position and a sitting position. That is, the state includes the presence/absence and the position. Also, the position includes the lying position and the sitting position.

After determining the state of the living body, the control section 20 performs determination result output processing to output a determination result (step S5). The determination result output processing in step S5 is processing to transmit information on the determination result from the communication section 27 to the communication device 3 via the communication network NW.

The communication device 3 receives, by the communication section 30, the information on the determination result transmitted from the state determination device 2 via the communication network NW. The communication device 3 outputs, from the output section 31, the received information on the determination result. The output of the determination result is performed as report processing such as light output, image display, audio output, ringing, and vibrating, from various kinds of communication devices 3 such as a nurse call receiver carried by a nurse, a monitor equipped in the nurse's station, and a mobile phone carried by an external person involved. Thus, since the staff such as nurses, caregivers and doctors and/or the persons involved such as families can confirm the determination result that is output from the communication device 3, they can take appropriate measures according to the state of the object care recipient.

Specific Examples of Signal Processing

Figure 4:
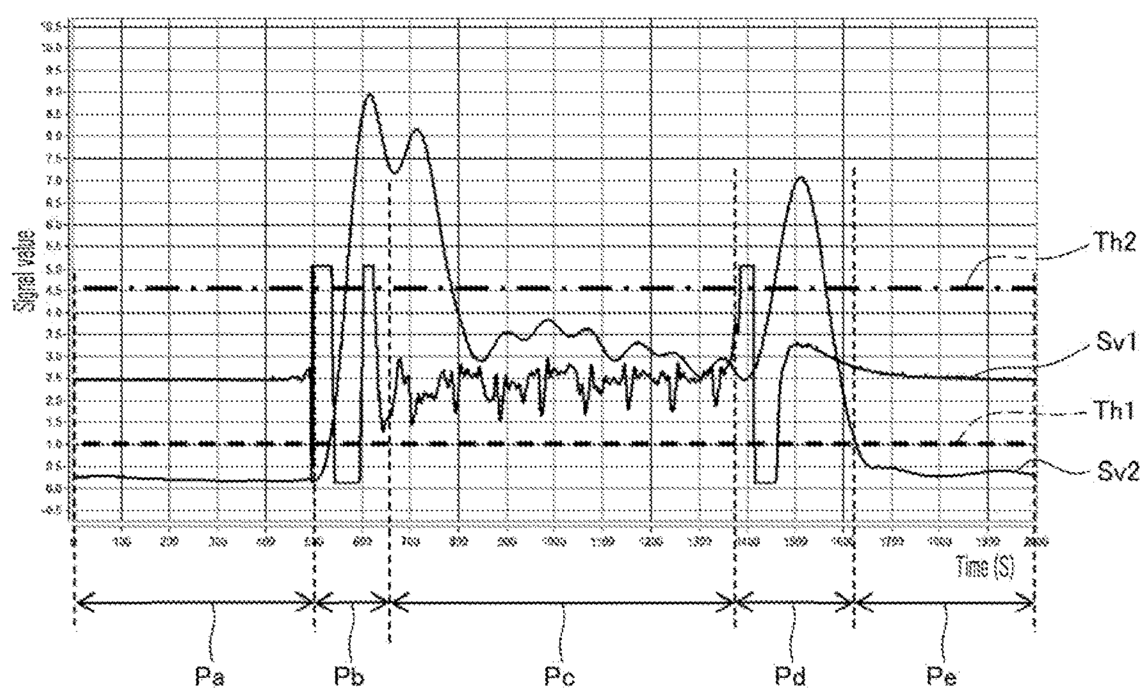
FIG. 4 is a graph indicating one example of electrical signal processed by the state determination device of the present invention.

Here, specific examples of signal processing will be described related to the rectification processing, the envelope detection processing, and the state determination processing executed by the state determination device 2. FIG. 4 is a graph indicating one example of the electrical signal processed by the state determination device 2 of the present invention. Also, FIG. 4 is a graph indicating general determination of the state of the care recipient by the state determination device 2. In FIG. 4, the graph is plotted with time as the horizontal axis and the signal value of the digital electrical signal after amplifying the voltage as the vertical axis, and indicates transition of the electrical signal for 20 seconds from a certain time point at a sampling interval of 10 ms. In FIG. 4, Sv1 represents the signal value after subjected to the A/D conversion processing in step S1, and Sv2 represents the signal value after subjected to the rectification processing in step S2 and the envelope detection processing in step S3. Furthermore in FIG. 4, Th1 represents a get-up determination threshold value and Th2 represents a bed-entry determination threshold value. The get-up determination threshold value Th1 and the bed-entry determination threshold value Th2 are threshold values recorded in order to be used for the state determination with respect to variation of the signal value plotted on the vertical axis. A period Pa, a period Pb, a period Pc, a period Pd and a period Pe are plotted on the horizontal axis of the graph in FIG. 4. These periods represent respective periods of time corresponding to the states of the position of the care recipient. In FIG. 4, the period Pa is a period of time when the care recipient is absent (not on the bed), the period Pb is a period of time when the care recipient gets into bed (takes the bed-entry motion), the period Pc is a period of time when the care recipient is taking a lying position after getting into bed, the period Pd is a period of time when the care recipient gets up on the bed from the lying position, and the period Pe is a period of time when the care recipient sits up in the bed and is taking a sitting position. The signal value Sv1 reflects, in the period Pc, various kinds of vibrations generated by the care recipient in the lying position such as vibrations by heartbeat, vibrations by lung breathing, and vibrations by physical movement. The signal value Sv1 considerably varies in the period Pb when the care recipient takes the bed-entry motion as well as in the period Pd when the care recipient gets up on the bed, and stabilizes in the period Pe when the care recipient is in the sitting position. Also, the signal value Sv2 captures general changes of the signal value Sv1 in the period Pa, the period Pb, the period Pc, the period Pd and the period Pe. The state determination device 2 determines the state of the care recipient by comparing the signal value Sv2 to the get-up determination threshold value Th1 and the bed-entry determination threshold value Th2. In the example shown in FIG. 4, when the signal value Sv2 is continuously smaller than the get-up determination threshold value Th1 after it is determined that the care recipient is absent, it is determined that the care recipient is still absent. When the signal value Sv2 becomes larger than the get-up determination threshold value Th1 and also larger than the bed-entry determination threshold value Th2 after it is determined that the care recipient is absent, it is determined that the care recipient takes the bed-entry motion. When the signal value Sv2 becomes larger than the get-up determination threshold value Th1 but smaller than the bed-entry determination threshold value Th2 after it is determined that the care recipient takes the bed-entry motion, it is determined that the care recipient is in the lying position. When the signal value Sv2 becomes smaller than the get-up determination threshold value Th1 after it is determined that the care recipient is in the lying position, it is determined that the care recipient takes the sitting position.

Figure 5:
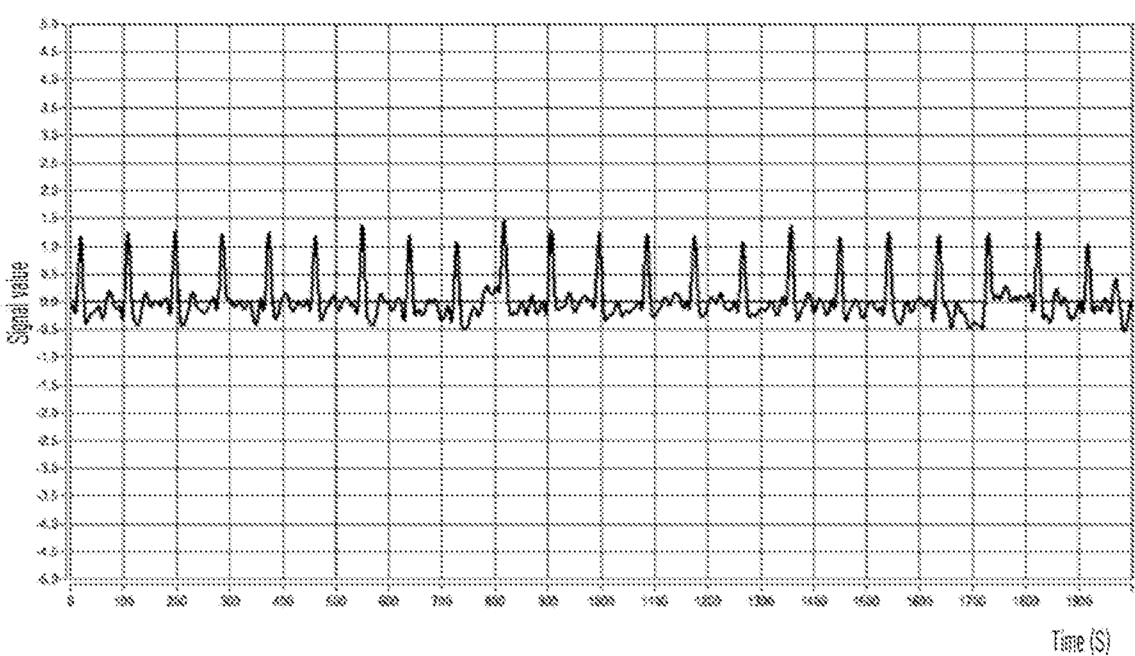
FIG. 5 is a graph indicating one example of electrical signal processed by the state determination device of the present invention.
Figure 6:
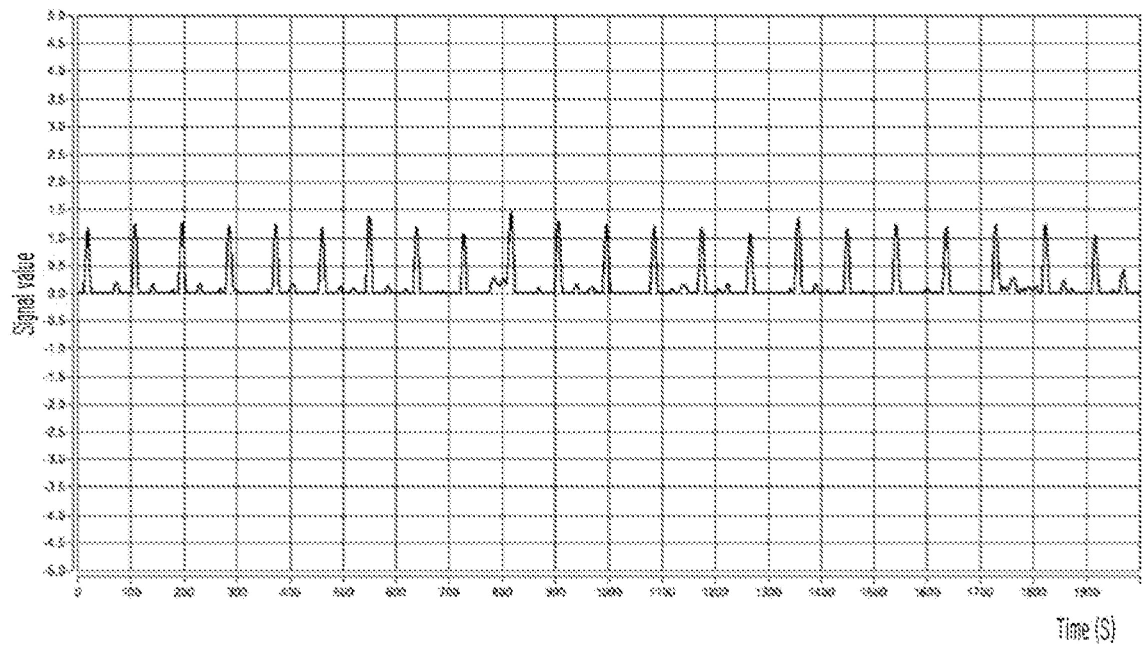
FIG. 6 is a graph indicating one example of electrical signal processed by the state determination device of the present invention.

The specific examples of the signal processing in the respective steps will be further described. FIGS. 5 and 6 are graphs each indicating one example of the electrical signal processed by the state determination device 2 of the present invention. In FIGS. 5 and 6, each graph is plotted with time as the horizontal axis and the signal value of the digital electrical signal after amplifying the voltage as the vertical axis, and indicates transition of the electrical signal for 20 seconds from a certain time point at a sampling interval of 10 ms. Each graph exemplarily shown in FIGS. 5 and 6 indicates signal when the care recipient is in the lying position, which corresponds to the state in the period Pc in FIG. 4. In FIG. 5, the graph indicates the signal value after subjected to the A/D conversion processing in step S1, and in FIG. 6, the graph indicates the signal value after the signal value in FIG. 5 is subjected to the half-wave rectification as the rectification processing in step S2. As can be clearly seen from the comparison of FIG. 5 and FIG. 6, there exist negative signal values in FIG. 5, which are all zero "0" in FIG. 6. Thus, it is obvious that the half-wave rectification has been performed. The state determination device 2 can execute, as the rectification processing in step S2, the half-wave rectification shown in FIGS. 5 and 6.

Figure 7:
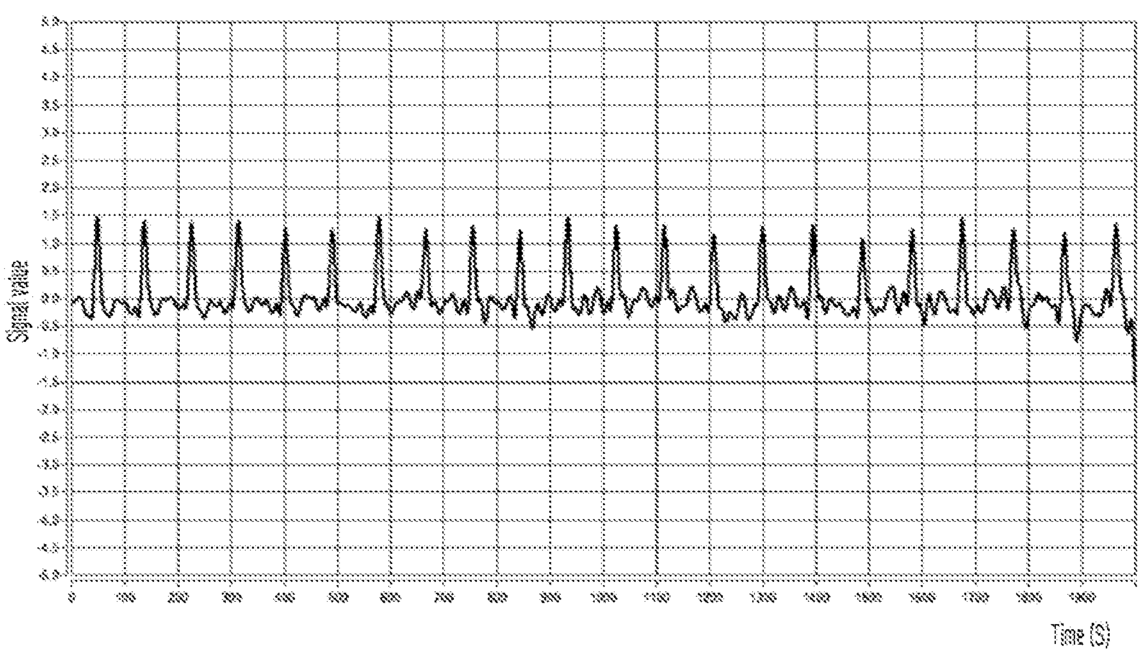
FIG. 7 is a graph indicating one example of electrical signal processed by the state determination device of the present invention.
Figure 8:
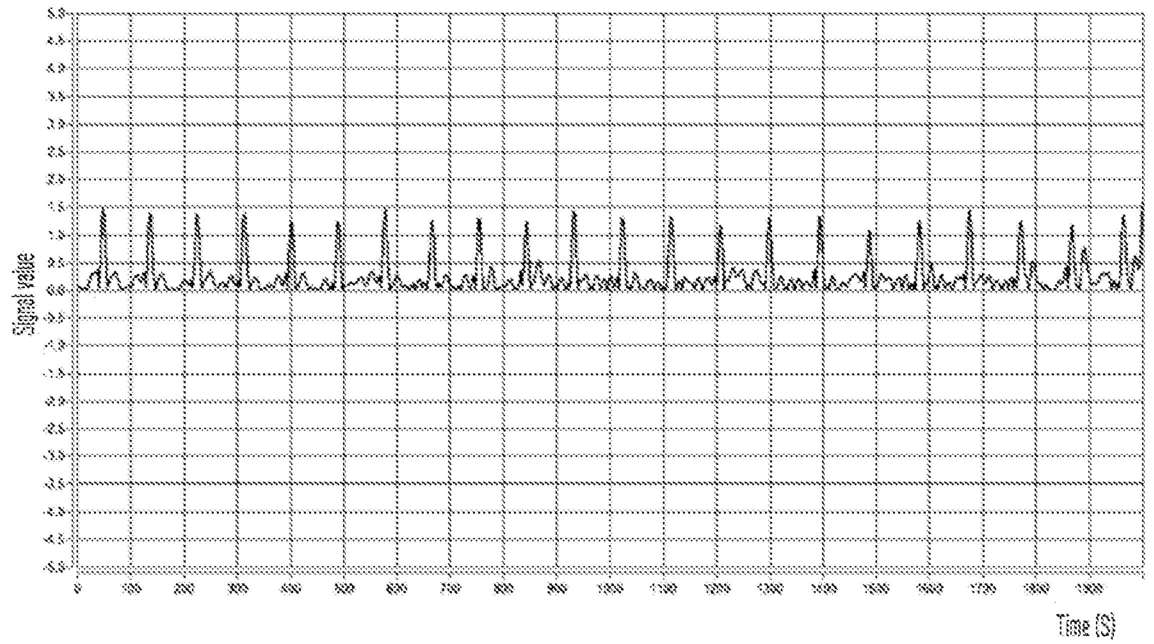
FIG. 8 is a graph indicating one example of electrical signal processed by the state determination device of the present invention.

FIGS. 7 and 8 are graphs each indicating one example of the electrical signal processed by the state determination device 2 of the present invention. In FIGS. 7 and 8, each graph is plotted with time as the horizontal axis and the signal value of the digital electrical signal after amplifying the voltage as the vertical axis, and indicates transition of the electrical signal for 20 seconds from a certain time point at a sampling interval of 10 ms. Each graph exemplarily shown in FIGS. 7 and 8 indicates signal when the care recipient is in the lying position, which corresponds to the state in the period Pc in FIG. 4. In FIG. 7, the graph indicates the signal value after subjected to the A/D conversion processing in step S1, and in FIG. 8, the graph indicates the signal value after the signal value in FIG. 7 is subjected to the full-wave rectification as the rectification processing in step S2. As can be clearly seen from the comparison of FIG. 7 and FIG. 8, there exist negative signal values in FIG. 7, which are inverted to be positive values in FIG. 8. Thus, it is obvious that the full-wave rectification has been performed. The state determination device 2 can execute, as the rectification processing in step S2, the full-wave rectification shown in FIGS. 7 and 8.

Figure 9:
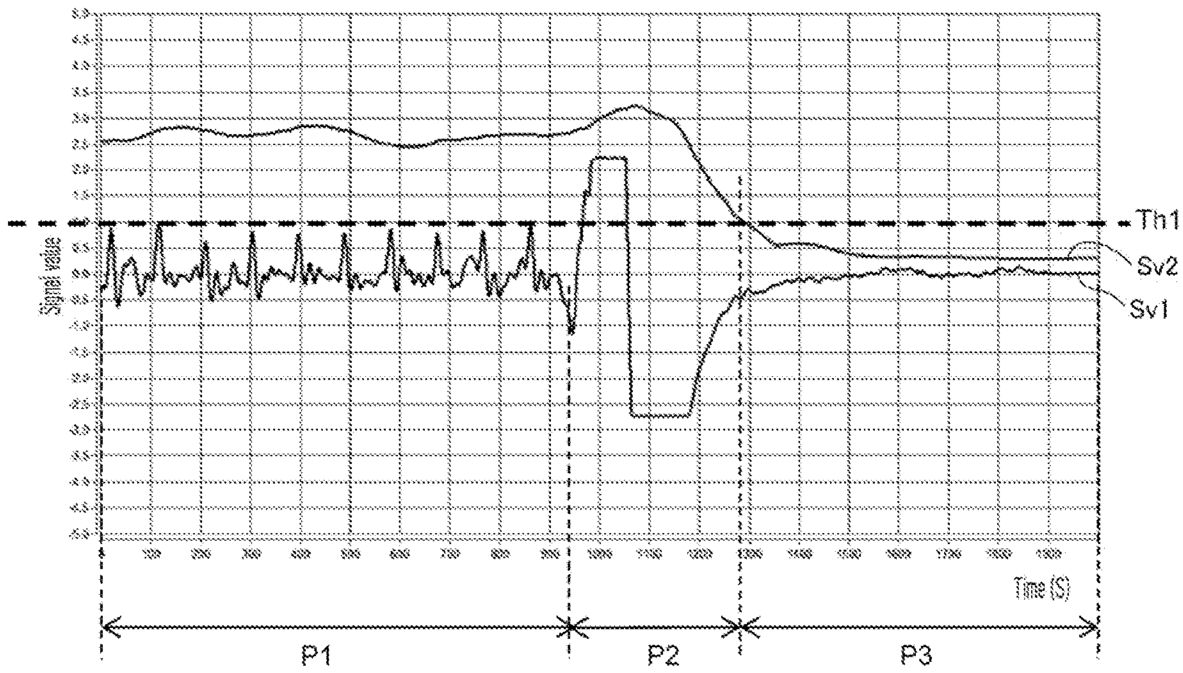
FIG. 9 is a graph indicating one example of electrical signal processed by the state determination device of the present invention.

FIG. 9 is a graph indicating one example of the electrical signal processed by the state determination device 2 of the present invention. In FIG. 9, the graph is plotted with time as the horizontal axis and the signal value of the digital electrical signal after amplifying the voltage as the vertical axis, and indicates transition of the electrical signal for 20 seconds from a certain time point at a sampling interval of 10 ms. In FIG. 9, Sv1 represents the signal value after subjected to the A/D conversion processing in step S1, and Sv2 represents the signal value after subjected to the rectification processing in step S2 and the envelope detection processing in step S3. In FIG. 9, the signal value Sv2 is exemplarily indicated, which is smoothed by the moving-average processing as the envelope detection processing in step S3. As the moving-average processing, the average is taken of the latest 100 samples. Then, the state determination device 2 compares the signal value Sv2 after subjected to the envelope detection processing to the get-up determination threshold value Th1 as the state determination processing in step S4. Thus, it is determined whether the signal value Sv2 is larger or smaller than the get-up determination threshold value Th1 so as to determine the position of the care recipient. In the example shown in FIG. 9, when the signal value Sv2 is larger than the get-up determination threshold value Th1, it is determined that the care recipient is not in the sitting position but in the lying position. When the signal value Sv2 is smaller than the get-up determination threshold value Th1, it is determined that the care recipient is in the sitting position. Therefore, in the example shown in FIG. 9, it is determined that the care recipient is in the lying position (not in the sitting position) in the period P1, while it is determined that the care recipient gets up and takes the sitting position in the period P3.

Figure 10:
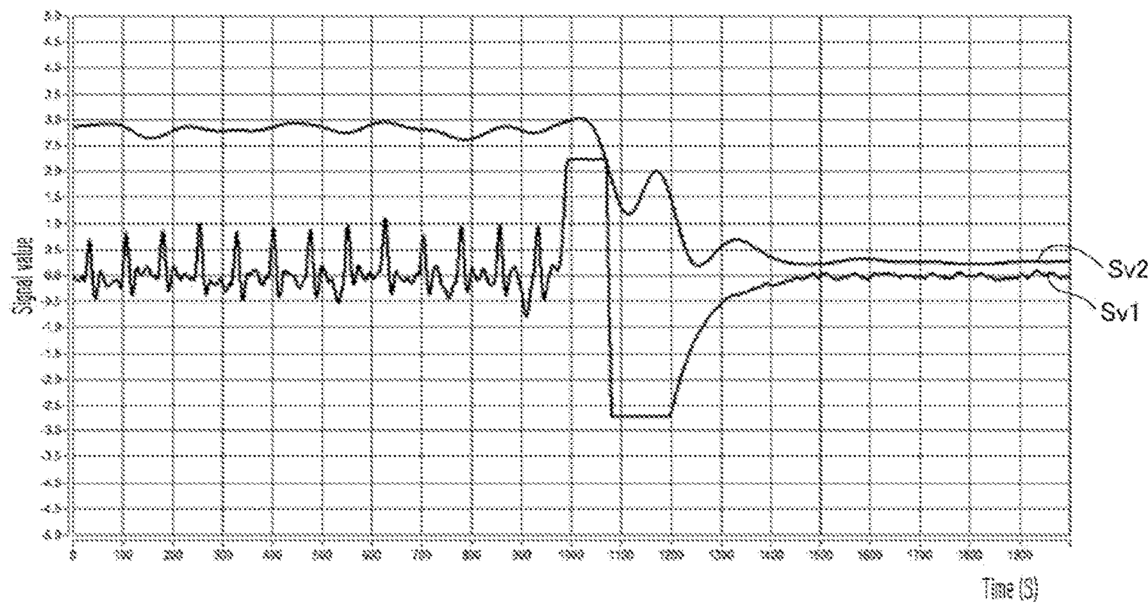
FIG. 10 is a graph indicating one example of electrical signal processed by the state determination device of the present invention.

FIG. 10 is a graph indicating one example of the electrical signal processed by the state determination device 2 of the present invention. In FIG. 10, the graph is plotted with time as the horizontal axis and the signal value of the digital electrical signal after amplifying the voltage as the vertical axis, and indicates transition of the electrical signal for 20 seconds from a certain time point at a sampling interval of 10 ms. In FIG. 10, Sv1 represents the signal value after subjected to the A/D conversion processing in step S1, and Sv2 represents the signal value after subjected to the rectification processing in step S2 and the envelope detection processing in step S3. In FIG. 10, the signal value Sv2 is exemplarily indicated, which is smoothed by the LPF processing as the envelope detection processing in step S3. In the LPF processing exemplarily shown in FIG. 10, the digital electrical signal at the frequency band not more than 0.5 Hz is allowed to pass while the digital electrical signal at the frequency band more than 0.5 Hz is cutoff. Even when the signal value is smoothed by the LPF processing, decrease of the signal value Sv2 appears when the care recipient changes the position from the lying position to the sitting position. Therefore, in this case also, it is possible to determine the state of the care recipient by setting appropriately the get-up determination threshold value Th1.

Figure 11:
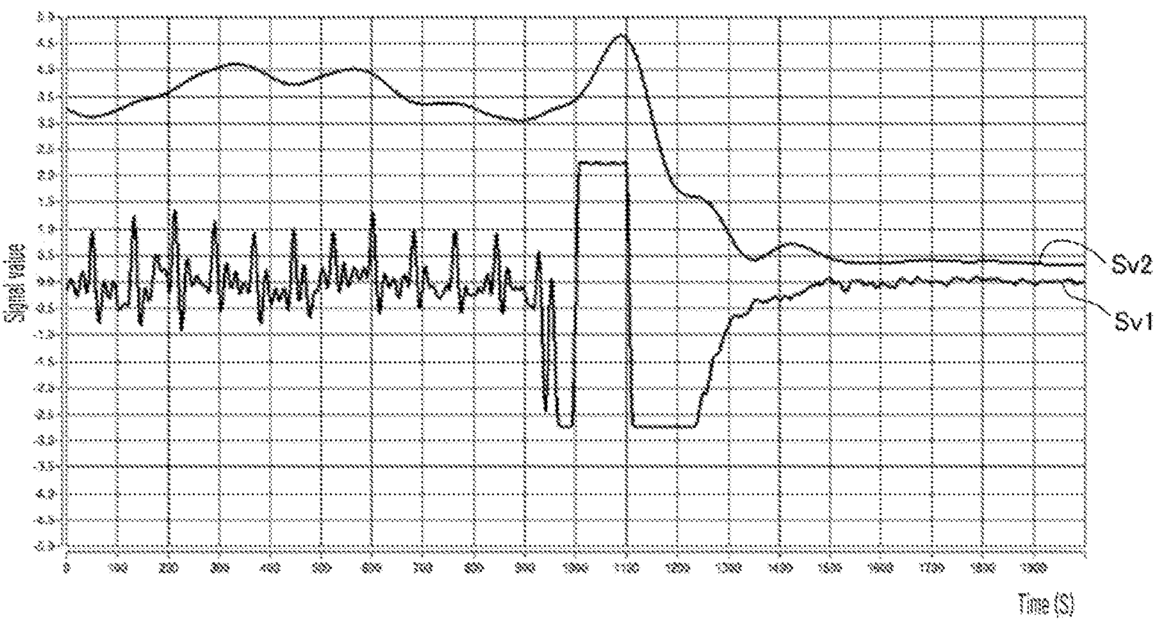
FIG. 11 is a graph indicating one example of electrical signal processed by the state determination device of the present invention.

FIG. 11 is a graph indicating one example of the electrical signal processed by the state determination device 2 of the present invention. In FIG. 11, the graph is plotted with time as the horizontal axis and the signal value of the digital electrical signal after amplifying the voltage as the vertical axis, and indicates transition of the electrical signal for 20 seconds from a certain time point at a sampling interval of 10 ms. In FIG. 11, Sv1 represents the signal value after subjected to the A/D conversion processing in step S1, and Sv2 represents the signal value after subjected to the rectification processing in step S2 and the envelope detection processing in step S3. In FIG. 11, the signal value Sv2 is exemplarily indicated, which is smoothed by processing combining the moving-average processing and the LPF processing as the envelope detection processing in step S3. In the envelope detection processing exemplarily shown in FIG. 11, the signal value Sv2 is derived as the envelope by calculating the moving average of the latest 100 samples of the digital electrical signal at the frequency band not more than 0.5 Hz, which is allowed to pass by the LPF processing. Even when the moving-average processing and the LPF processing are combined as the envelope detection processing, decrease of the signal value Sv2 appears when the care recipient changes the position from the lying position to the sitting position. Therefore, in this case also, it is possible to determine the state of the care recipient by setting appropriately the get-up determination threshold value Th1.

Figure 12:
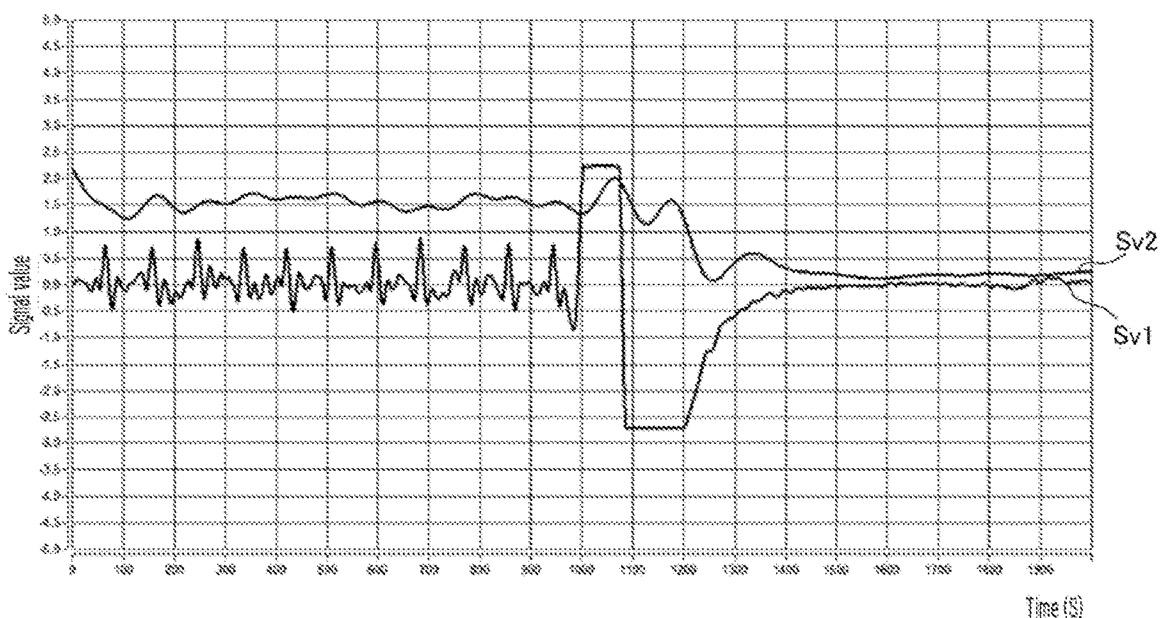
FIG. 12 is a graph indicating one example of electrical signal processed by the state determination device of the present invention.

FIG. 12 is a graph indicating one example of the electrical signal processed by the state determination device 2 of the present invention. In FIG. 12, the graph is plotted with time as the horizontal axis and the signal value of the digital electrical signal after amplifying the voltage as the vertical axis, and indicates transition of the electrical signal for 20 seconds from a certain time point at a sampling interval of 10 ms. In FIG. 12, Sv1 represents the signal value after subjected to the A/D conversion processing in step S1, and Sv2 represents the signal value after subjected to the rectification processing in step S2 and the envelope detection processing in step S3. In FIG. 12, the signal value Sv2 is exemplarily indicated, which is smoothed by the BPF processing as the envelope detection processing in step S3. In the BPF processing exemplarily shown in FIG. 12, the digital electrical signal at the frequency band of 0.1 to 0.5 Hz is allowed to pass while the digital electrical signal at the frequency band other than the above is cutoff. Even when the signal value is smoothed by the BPF processing, decrease of the signal value Sv2 appears when the care recipient changes the position from the lying position to the sitting position. Therefore, in this case also, it is possible to determine the state of the care recipient by setting appropriately the get-up determination threshold value Th1.

Figure 13:
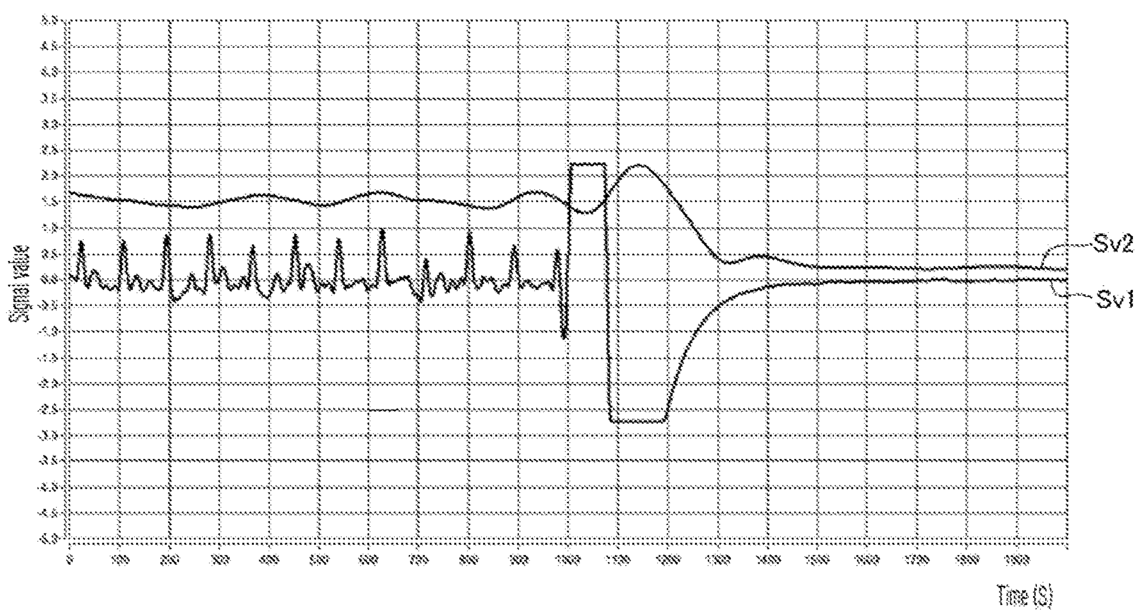
FIG. 13 is a graph indicating one example of electrical signal processed by the state determination device of the present invention.

FIG. 13 is a graph indicating one example of the electrical signal processed by the state determination device 2 of the present invention. In FIG. 13, the graph is plotted with time as the horizontal axis and the signal value of the digital electrical signal after amplifying the voltage as the vertical axis, and indicates transition of the electrical signal for 20 seconds from a certain time point at a sampling interval of 10 ms. In FIG. 13, Sv1 represents the signal value after subjected to the A/D conversion processing in step S1, and Sv2 represents the signal value after subjected to the rectification processing in step S2 and the envelope detection processing in step S3. In FIG. 13, the signal value Sv2 is exemplarily indicated, which is smoothed by processing combining the moving-average processing and the BPF processing as the envelope detection processing in step S3. In the envelope detection processing exemplarily shown in FIG. 13, the signal value Sv2 is derived as the envelope by calculating the moving average of the latest 100 samples of the digital electrical signal at the frequency band of 0.1 to 0.5 Hz, which is allowed to pass by the BPF processing. Even when the moving-average processing and the BPF processing are combined as the envelope detection processing, decrease of the signal value Sv2 appears when the care recipient changes the position from the lying position to the sitting position. Therefore, in this case also, it is possible to determine the state of the care recipient by setting appropriately the get-up determination threshold value Th1.

Figure 14:
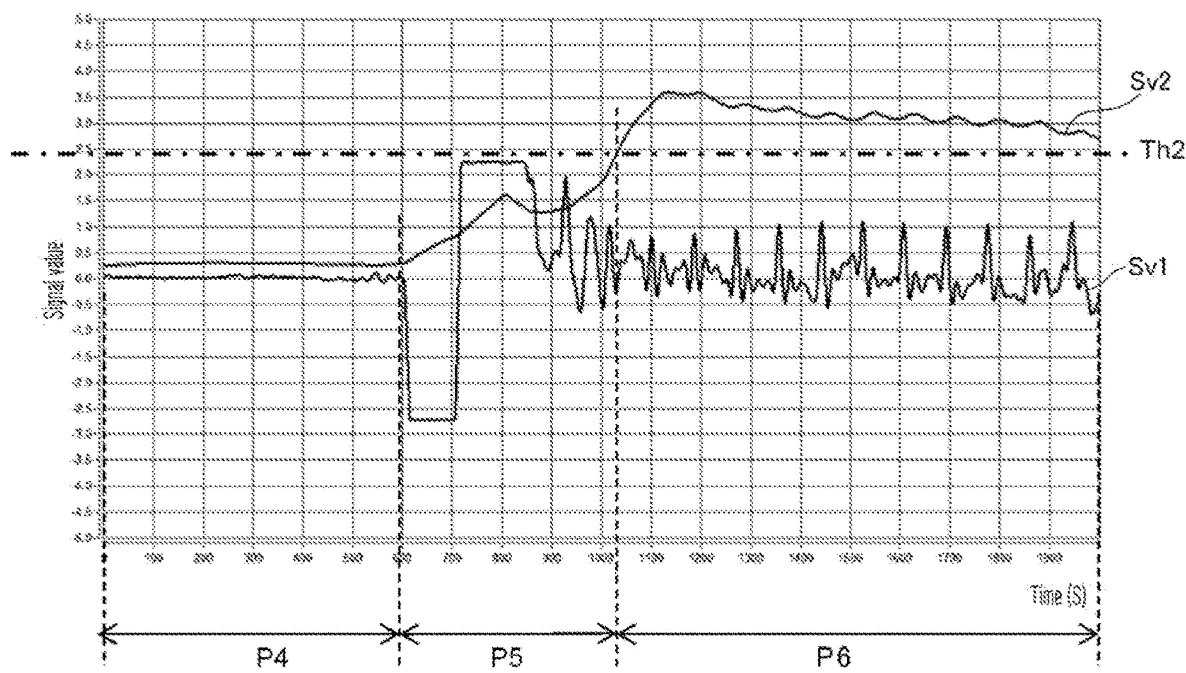
FIG. 14 is a graph indicating one example of electrical signal processed by the state determination device of the present invention.

The state determination device 2 of the present invention for determining the state of the care recipient can determine not only the position on the bed but also whether the care recipient is present or absent. Here, one example of the signal processing will be described in the case where the determination of the presence/absence of the care recipient is performed. FIG. 14 is a graph indicating one example of the electrical signal processed by the state determination device 2 of the present invention. In FIG. 14, the graph is plotted with time as the horizontal axis and the signal value of the digital electrical signal after amplifying the voltage as the vertical axis, and indicates transition of the electrical signal for 20 seconds from a certain time point at a sampling interval of 10 ms. In FIG. 14, Sv1 represents the signal value after subjected to the A/D conversion processing in step S1, and Sv2 represents the signal value after subjected to the rectification processing in step S2 and the envelope detection processing in step S3. In FIG. 14, the signal value Sv2 is exemplarily indicated, which is smoothed by the moving-average processing as the envelope detection processing in step S3. As the moving-average processing, the average is taken of the latest 100 samples. Also, Th2 in FIG. 14 represents the bed-entry determination threshold value. A period P4, a period P5 and a period P6 are plotted on the horizontal axis of the graph in FIG. 14. These periods represent respective periods of time corresponding to the presence/absence and the states of the position of the care recipient. In FIG. 14, the period P4 is a period of time when the care recipient is absent (not on the bed), the period P5 is a period of time when the care recipient gets into bed (takes the bed-entry motion), and the period P6 is a period of time when the care recipient is taking a lying position after getting into bed. Then, the state determination device 2 compares the signal value Sv2 after subjected to the envelope detection processing to the bed-entry determination threshold value Th2 as the state determination processing in step S4. Thus, it is determined whether the signal value Sv2 is larger or smaller than the bed-entry determination threshold value Th2 so as to determine the presence/absence and the state of the care recipient. In the example shown in FIG. 14, when the signal value Sv2 is continuously smaller than the bed-entry determination threshold value Th2 for a predetermined period of time after it is determined that the care recipient is absent, it is determined that the care recipient is still absent. Also, when the signal value Sv2 changes from the value smaller than the bed-entry determination threshold value Th2 to the value larger than the bed-entry determination threshold value Th2, and furthermore when this value Sv2 continues stably for a predetermined period of time, it is determined that the care recipient gets into bed and is in the lying position.

Figure 15:
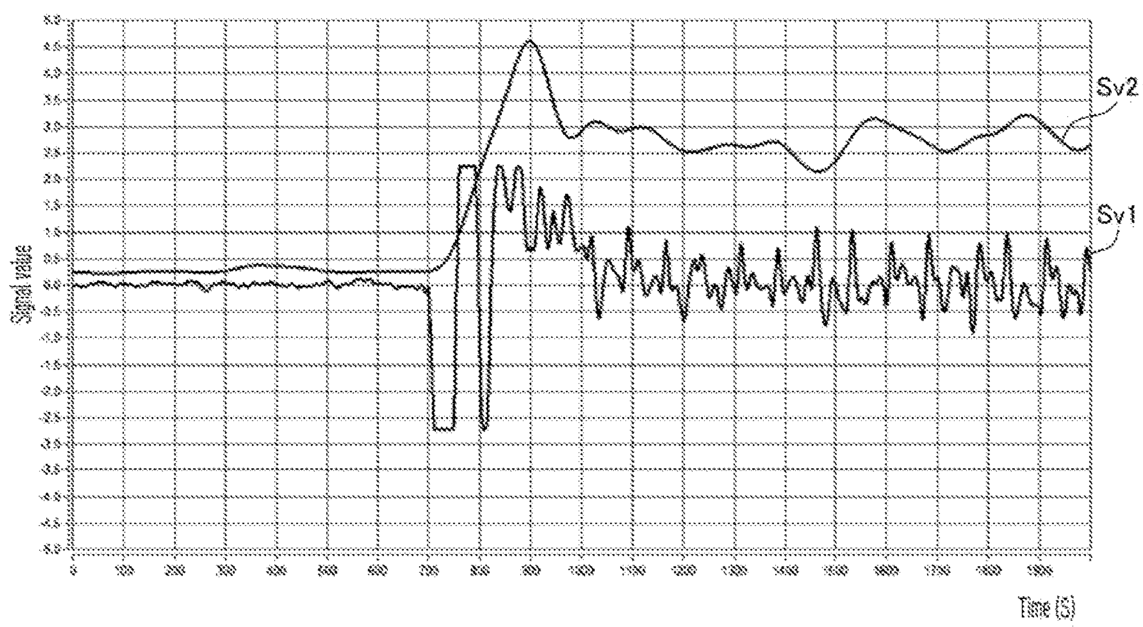
FIG. 15 is a graph indicating one example of electrical signal processed by the state determination device of the present invention.

FIG. 15 is a graph indicating one example of the electrical signal processed by the state determination device 2 of the present invention. In FIG. 15, the graph is plotted with time as the horizontal axis and the signal value of the digital electrical signal after amplifying the voltage as the vertical axis, and indicates transition of the electrical signal for 20 seconds from a certain time point at a sampling interval of 10 ms. In FIG. 15, Sv1 represents the signal value after subjected to the A/D conversion processing in step S1, and Sv2 represents the signal value after subjected to the rectification processing in step S2 and the envelope detection processing in step S3. In FIG. 15, the signal value Sv2 is exemplarily indicated, which is smoothed by the LPF processing as the envelope detection processing in step S3. In the LPF processing exemplarily shown in FIG. 15, the digital electrical signal at the frequency band not more than 0.5 Hz is allowed to pass while the digital electrical signal at the frequency band more than 0.5 Hz is cutoff. Even when the signal value is smoothed by the LPF processing, increase of the signal value Sv2 appears when the care recipient gets into bed and takes the lying position. Therefore, in this case also, it is possible to determine the state of the care recipient by setting appropriately the bed-entry determination threshold value Th2.

Figure 16:
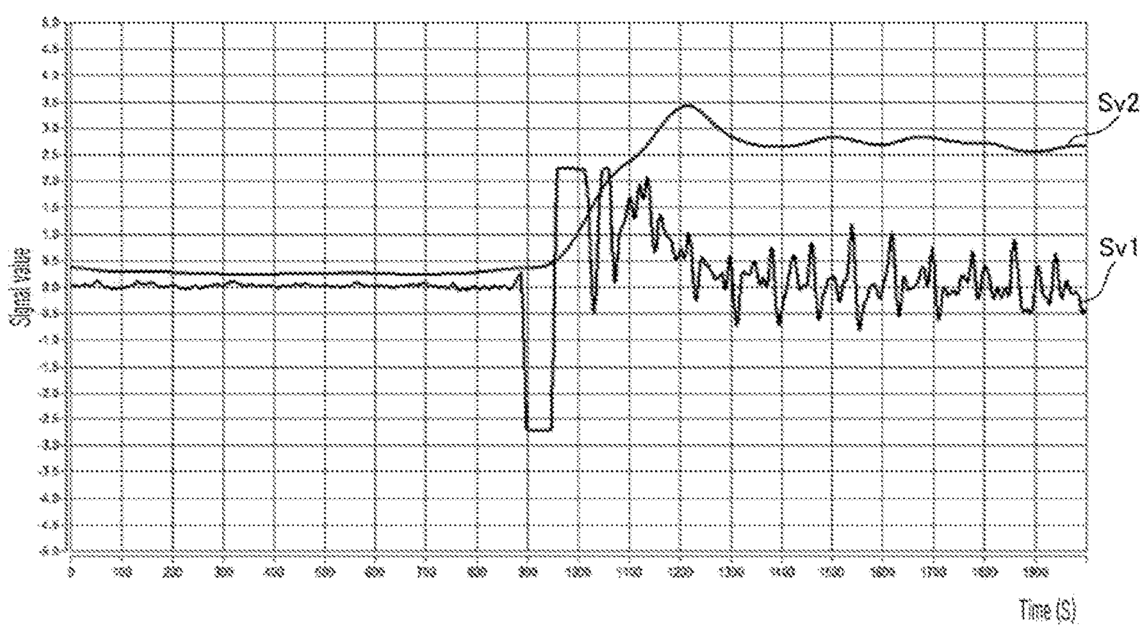
FIG. 16 is a graph indicating one example of electrical signal processed by the state determination device of the present invention.

FIG. 16 is a graph indicating one example of the electrical signal processed by the state determination device 2 of the present invention. In FIG. 16, the graph is plotted with time as the horizontal axis and the signal value of the digital electrical signal after amplifying the voltage as the vertical axis, and indicates transition of the electrical signal for 20 seconds from a certain time point at a sampling interval of 10 ms. In FIG. 16, Sv1 represents the signal value after subjected to the A/D conversion processing in step S1, and Sv2 represents the signal value after subjected to the rectification processing in step S2 and the envelope detection processing in step S3. In FIG. 16, the signal value Sv2 is exemplarily indicated, which is smoothed by processing combining the moving-average processing and the LPF processing as the envelope detection processing in step S3. In the envelope detection processing exemplarily shown in FIG. 16, the signal value Sv2 is derived as the envelope by calculating the moving average of the latest 100 samples of the digital electrical signal at the frequency band not more than 0.5 Hz, which is allowed to pass by the LPF processing. Even when the moving-average processing and the LPF processing are combined as the envelope detection processing, increase of the signal value Sv2 appears when the care recipient gets into bed and takes the lying position. Therefore, in this case also, it is possible to determine the state of the care recipient by setting appropriately the bed-entry determination threshold value Th2.

Figure 17:
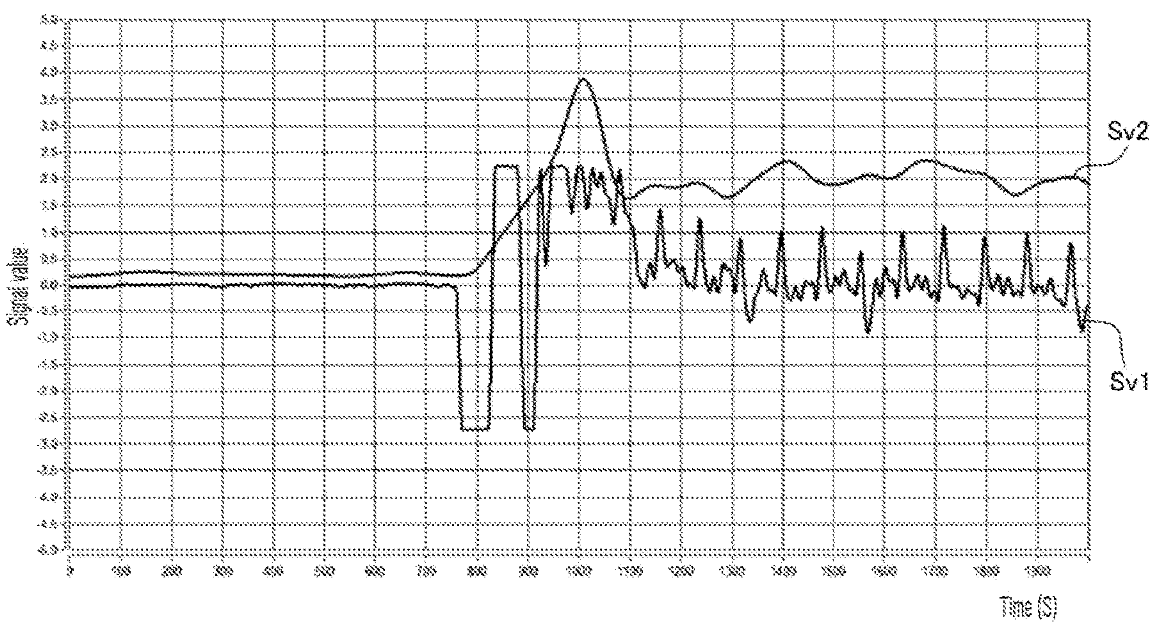
FIG. 17 is a graph indicating one example of electrical signal processed by the state determination device of the present invention.

FIG. 17 is a graph indicating one example of the electrical signal processed by the state determination device 2 of the present invention. In FIG. 17, the graph is plotted with time as the horizontal axis and the signal value of the digital electrical signal after amplifying the voltage as the vertical axis, and indicates transition of the electrical signal for 20 seconds from a certain time point at a sampling interval of 10 ms. In FIG. 17, Sv1 represents the signal value after subjected to the A/D conversion processing in step S1, and Sv2 represents the signal value after subjected to the rectification processing in step S2 and the envelope detection processing in step S3. In FIG. 17, the signal value Sv2 is exemplarily indicated, which is smoothed by the BPF processing as the envelope detection processing in step S3. In the BPF processing exemplarily shown in FIG. 17, the digital electrical signal at the frequency band of 0.1 to 0.5 Hz is allowed to pass while the digital electrical signal at the frequency band other than the above is cutoff. Even when the signal value is smoothed by the BPF processing, increase of the signal value Sv2 appears when the care recipient gets into bed and takes the lying position. Therefore, in this case also, it is possible to determine the state of the care recipient by setting appropriately the bed-entry determination threshold value Th2.

Figure 18:
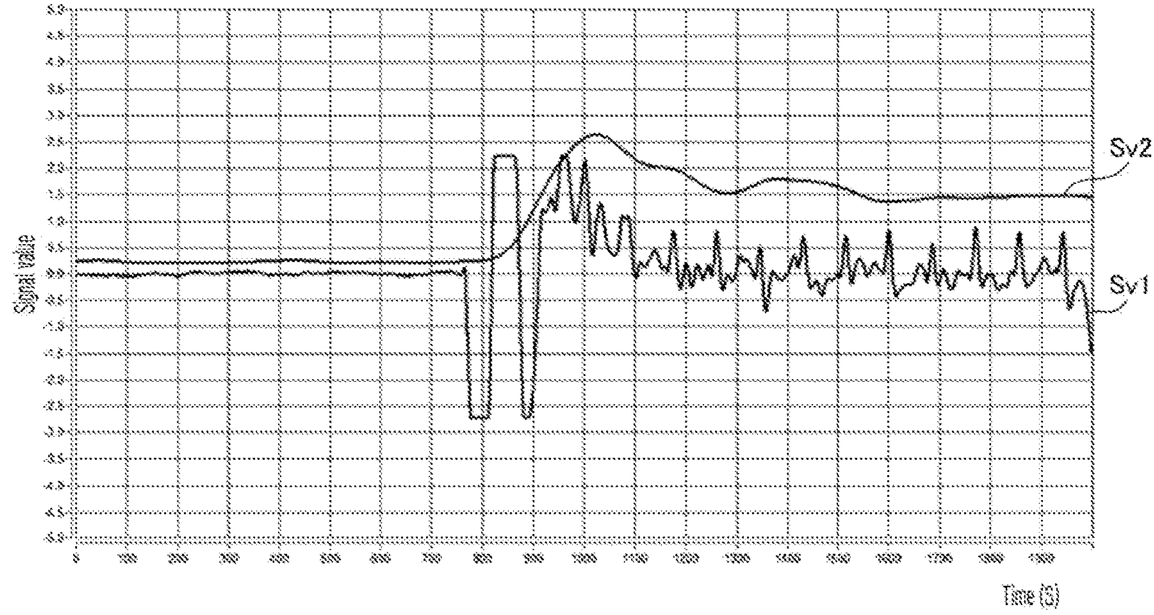
FIG. 18 is a graph indicating one example of electrical signal processed by the state determination device of the present invention.

FIG. 18 is a graph indicating one example of the electrical signal processed by the state determination device 2 of the present invention. In FIG. 18, the graph is plotted with time as the horizontal axis and the signal value of the digital electrical signal after amplifying the voltage as the vertical axis, and indicates transition of the electrical signal for 20 seconds from a certain time point at a sampling interval of 10 ms. In FIG. 18, Sv1 represents the signal value after subjected to the A/D conversion processing in step S1, and Sv2 represents the signal value after subjected to the rectification processing in step S2 and the envelope detection processing in step S3. In FIG. 18, the signal value Sv2 is exemplarily indicated, which is smoothed by processing combining the moving-average processing and the BPF processing as the envelope detection processing in step S3. In the envelope detection processing exemplarily shown in FIG. 18, the signal value Sv2 is derived as the envelope by calculating the moving average of the latest 100 samples of the digital electrical signal at the frequency band of 0.1 to 0.5 Hz, which is allowed to pass by the BPF processing. Even when the moving-average processing and the BPF processing are combined as the envelope detection processing, increase of the signal value Sv2 appears when the care recipient gets into bed and takes the lying position. Therefore, in this case also, it is possible to determine the state of the care recipient by setting appropriately the bed-entry determination threshold value Th2.

As described above, the state determination device 2 of the present invention acquires the electrical signal according to the detected vibration so as to determine the state of the living body such as the presence/absence and the position based on the envelope derived from the acquired electrical signal. In this way, in the case where the determination device 2 is applied, for example, to determination of the state of the care recipient in the facility, it is possible to determine the state of the care recipient and to notify the caregiver of the determined state even when the caregiver does not present in the room. Accordingly, when the care recipient may be in the abnormal state, the caregiver can immediately address the situation, which is an excellent effect of the present invention.

The present invention should not be limited by the foregoing embodiment, and may be embodied in other forms without departing from the gist or essential characteristics thereof. Therefore, the embodiments described herein are to be considered in all respects as illustrative and not limiting. The scope of the present invention is indicated by the appended claims rather than by the foregoing embodiments, and all modifications and changes that come within the meaning and range of equivalency of the claims are intended to be embraced therein.

For example, in the forgoing embodiment, only the cases are exemplarily described, in which the signal value is larger than or smaller than the get-up determination threshold value Th1 and/or the bed-entry determination threshold value Th2. However, the present invention is not limited thereto. Other determination threshold values and/or other determination methods may be appropriately set. For example, in order to determine the state such as the lying position and the sitting position, it is possible to set another determination condition whether the signal value remains, for a certain period of time, larger than or smaller than the determination threshold value(s) such as the get-up determination threshold value Th1 and/or the bed-entry determination threshold value Th2. In this way, it is possible to reduce an erroneous notification because the determination is performed after the state has been certainly changed.

Furthermore, in the foregoing embodiment, when the amplitude amplification section 11 amplifies the voltage of the analog electrical signal according to the vibration, the amplification degree may be adjusted relative to the magnitude of vibration that depends on variable factors such as the thickness of the mattress and an individual difference of the care recipient, so that a certain voltage amplitude can be output. That is, the state determination device 2 can adjust the amplification rate according to the living body whose state is determined and/or the environment under which the state is determined. In this way, it is possible for each determination value (i.e. the get-up determination threshold value Th1 and the bed-entry determination threshold value Th2) to have one value without being changed for every variable factor. Thus, it is not required to change the determination threshold value depending on the variable factors such as the environment in which the sensor is installed and an individual difference of the care recipient.

Also in the foregoing embodiment, the get-up determination threshold value Th1 and the bed-entry determination threshold value Th2 are exemplarily indicated each as a fixed threshold value. However, the present invention is not limited thereto. These determination threshold values may be changed for a predetermined period of time according to the motion of the care recipient. As one example, the get-up determination threshold value Th1 may be shifted to a larger value for a predetermined period of time after the signal value Sv1, which is already subjected to the A/D conversion processing in step S1, becomes larger than a certain threshold value. When there is a big motion of the care recipient by getting up on the bed from the lying position or by a body movement, the signal value Sv1 increases, and in association with this increase, the signal value Sv2 also increases. Thus, a certain period of time may be needed for the signal value Sv2 to decrease after the care recipient gets up, which may cause delay of the get-up determination. Thus, when there is a big motion as above that results in the signal value Sv1 larger than the certain threshold value, the get-up determination threshold value Th1 can be shifted to a larger value for a predetermined period of time. With this configuration, it is possible to perform the get-up determination earlier than the conventional case in which the get-up determination threshold value Th1 is fixed.

Also in the foregoing embodiment, the determination of the state of the living body such as the presence/absence and the position is performed based on only the envelope derived from the acquired electrical signal according to the detected vibration. However, the present invention is not limited thereto. The biological information detected by the biological information detection device 4 may be used to determine the state along with the envelope. The biological information includes a heart rate, a respiratory rate, and a pulse. As one example, in addition to the bed-entry determination based on the envelope derived from the detection by the vibration detection device 1, the heart rate is also detected so as to confirm the bed-entry. Thus, it is possible to confirm the bed-entry state with higher accuracy.

Also, the respective values in the foregoing embodiment are all exemplarily indicated. The respective values such as the sampling interval, the sampling number in the moving-average processing, the frequency band in the LPF/BPF processing, and the threshold value may be appropriately set according to the embodiment.

Also in the foregoing embodiment, the states are exemplarily described, in which the care recipient gets up from the lying position to be in the sitting position, and in which the care recipient takes the lying position from the absent state. However, the present invention is not limited to thereto. That is, by recording the states and setting appropriate threshold values, the state determination device 2 of the present invention can detect changes in the state according to various situations in which, for example, the care recipient takes the lying position from the sitting position, and becomes absent from the sitting position.

Also in the foregoing embodiment, the vibration detection section 10 of the vibration detection device 1 is placed on the bed to determine the state of the care recipient. However, the present invention is not limited thereto, and can be applied to various situations. For example, the vibration detection device 1 can be used to determine the state of a driver who are sitting in the driver's seat of a vehicle, and thus prevent an abnormal state such as drowsy driving. Also in the present invention, the living body whose state is to be detected is not limited to human beings. The present invention can be applied to various cases, which includes, for example, the application to animals such as dogs or cats.

Also in the foregoing embodiment, the vibration detection device 1 includes the amplitude amplification section 11, and the state determination device 2 includes the A/D conversion section 22. However, the present invention is not limited thereto. The configurations of the respective devices may be designed as necessary. That is, the vibration detection device 1 may perform the A/D conversion processing to output the digital electrical signal. Also, the state determination device 2 may amplify the analog electrical signal. Furthermore, in place of the output section 31 of the communication device 3, the output section 26 of the state determination device 2 may perform the report processing to output the information on the determination result. In this way, the devices of the present invention may be appropriately designed.

Furthermore in the foregoing embodiment, the processing such as the rectification processing in step S2 and the envelope detection processing in step S3 is described as algorithm processing of the digital electrical signal. However, the present invention is not limited thereto. The processing may be realized as processing of the analog electrical signal by an analog electrical circuit. That is, the state determination device 2 of the present invention can perform the processing by combining electronic elements such as a diode, a resistor, and a capacitor. In this case, it is possible to omit the A/D conversion processing in step S1.

However, when the processing such as the rectification processing and the envelope detection processing is executed by an analog electrical circuit configured by combining the electronic elements such as a diode, a resistor, and a capacitor, there may occur a problem that does not appear in the algorithm processing. For example, in the analog electrical circuit, sometimes it is difficult to process the electrical signal having a voltage lower than the forward voltage of the diode that performs the rectification processing. Also, there may be a problem of accuracy in the rectification processing and the envelope detection processing to a minute voltage change detected by the vibration detection section 10. Furthermore, although the envelope detection processing such as the BPF processing and the LPF processing may also be performed by the analog electrical circuit configured by an electrical component such as an operational amplifier and by the electronic elements such as a resistor, a diode, and a capacitor, in this case there may be a problem of improvement in filter characteristics. Furthermore, in the analog electrical circuit, sometimes it is difficult to perform the moving-average processing as the envelope detection processing. Therefore, in the state determination system of the present invention, it is possible to build a further excellent system by configuring the system with the technique to process the digital electrical signal (i.e. elements, circuits, devices and the like).

Furthermore in the foregoing embodiment, the state of the care recipient is determined by real time. However, the present invention is not limited thereto, and can be applied to various situations. That is, in the state determination system of the present invention, the data may be recorded based on the detected vibration so that the change of the state of the care recipient may be determined and his/her behavior may be analyzed based on the recorded data at a later date.

DESCRIPTION OF REFERENCE NUMERALS

1 Vibration detection device
10 Vibration detection section
11 Amplitude amplification section
12 Output section
2 State determination device
20 Control section
21 Input section
22 A/D conversion section
23 Recording section
230 State determination program
24 Storage section
25 Operation section
26 Output section
27 Communication section
3 Communication device
30 Communication section
31 Output section
4 Biological information detection device
NW Communication network
REC Recording medium

The invention claimed is:

1. A state determination system for determining a state of a care recipient, the state determination system comprising:

a vibration detection device including a detection section using a sheet-like vibration sensor and an output section outputting an electrical signal according to a detected vibration by the detection device, the detection section being placed on an upper surface or a lower surface of a mattress of a bed used by care recipient; and a state determination device including a computer that includes a control section, a recording section, an input section that receives input of the electrical signal, and a communication section, wherein the recording section records a program to cause the computer to perform:

rectification processing to rectify the electrical signal;

envelope detection processing to derive an envelope from the rectified electrical signal; and determination processing to determine the state of the care recipient according to the derived envelope, the determination processing determines, as the state of the care recipient, a position of the care recipient from among a plurality of positions by comparing a value indicated by the derived envelope to a plurality of threshold values, the plurality of positions including at least a lying position and a sitting position, the plurality of predetermined threshold values includes (i) a bed-entry determination threshold value to determine a bed-entry motion of the care recipient and (ii) a get-up determination threshold value to determine a get-up motion of the care recipient who is in a bed, and the bed-entry determination threshold value is set to a value larger than the get-up determination threshold value, the state determination system further comprises a communication device communicably connected to the state determination device via a communication network, the communication section of the state determination device transmits information on the determined position of the care recipient to the communication device via the communication network, and the communication device includes an output section that outputs the received information determined position of the care recipient as at least any of: light output; image display; audio output; ringing; and vibrating.

2. The state determination system according to claim 1, wherein the determination processing determines that the care recipient is absent when the value indicated by the envelope remains smaller than the bed-entry determination threshold value and the get-up determination threshold value for a predetermined period of time, and the determination processing determines that the bed-entry motion is taken when the value indicated by the envelope becomes larger than the get-up determination threshold value and the bed-entry determination threshold value after it is determined that the care recipient is absent.

3. The state determination system according to claim 2, wherein the determination processing determines that the position of the care recipient is the lying position when the value indicated by the envelope becomes larger than the get-up determination threshold value and smaller than the bed-entry determination threshold value after it is determined that the care recipient takes the bed-entry motion, and the determination processing determines that the position of the care recipient is the sitting position when the value indicated by the envelope becomes smaller than the get-up determination threshold value after it is determined that the care recipient is in the lying position.

4. The state determination system according to claim 3, wherein the rectification processing converts the electrical signal into a pulsating current by half-wave rectification or full-wave rectification.

5. The state determination system according to claim 4, wherein the envelop detection processing includes any one of or any combination of: moving-average processing; BPF (band-pass filter) processing; and LPF (low-pass filter) processing.

6. The state determination system according to claim 1, wherein the vibration detection device further includes an amplitude amplification section, the amplitude amplification section is a signal amplifier that amplifies a voltage of the electrical signal, and the amplitude amplification section amplifies an analog electrical signal derived from the vibration.

7. The state determination system according to claim 1, wherein the vibration detection device further includes an A/D conversion section, the A/D conversion section is a converter that converts an analog electrical signal into a digital electrical signal, and the A/D conversion section performs A/D conversion processing to convert the analog electrical signal derived from the vibration into the digital electrical signal.

8. The state determination system according to claim 7, wherein the rectification processing rectifies the digital electrical signal, and the envelope detection processing derives the envelope from the rectified digital electrical signal.

9. The state determination system according to claim 1, further comprising an amplitude amplification section, wherein the amplitude amplification section is a signal amplifier that amplifies a voltage of the electrical signal, and the amplitude amplification section amplifies an analog electrical signal derived from the vibration.

10. The state determination system according to claim 1, wherein the state determination device further includes an A/D conversion section, the A/D conversion section is a converter that converts an analog electrical signal into a digital electrical signal, and the A/D conversion section performs A/D conversion processing to convert the analog electrical signal received and input from the vibration detection device.

11. The state determination system according to claim 10, wherein the rectification processing rectifies the digital electrical signal, and the envelope detection processing derives the envelope from the rectified digital electrical signal.

12. The state determination system according to claim 10, wherein the input section is an interface device that receives input of the analog electrical signal transmitted from the vibration detection device via a connection line.

13. The state determination system according to claim 1, wherein the communication device is any one of: a nurse call receiver; a monitor equipped in a nurse's station; and a mobile phone carried by an external person involved.

14. The state determination system according to claim 1, wherein the state determination system is equipped in any one of: a hospital; a nursing home; and a nursing facility.

15. The state determination system according to claim 1, further comprising a biological information detection device connectable to the state determination device, wherein the biological information detection device detects biological information on the care recipient, which is any one of: a heart rate, a respiratory rate and a pulse.

* * * * *